(12) United States Patent
Shurney et al.

(10) Patent No.: US 7,780,795 B1
(45) Date of Patent: Aug. 24, 2010

(54) ADHESIVE REMOVAL INDICATOR SYSTEM AND METHOD OF USE

(75) Inventors: Glenn A. Shurney, Chicago, IL (US); Yong C. Park, Lake Zurich, IL (US)

(73) Assignee: Universal Beauty, Inc., Elk Grove Village, IL (US)

( * ) Notice: Subject to any disclaimer, the term of this patent is extended or adjusted under 35 U.S.C. 154(b) by 0 days.

(21) Appl. No.: 12/633,583

(22) Filed: Dec. 8, 2009

(51) Int. Cl.
*B08B 7/04* (2006.01)

(52) U.S. Cl. .............. 134/26; 134/42; 134/38; 132/200; 132/201

(58) Field of Classification Search .......... 134/26, 134/38, 42; 132/200, 201
See application file for complete search history.

(56) References Cited

U.S. PATENT DOCUMENTS

| | | | |
|---|---|---|---|
| 4,807,649 A | 2/1989 | Eoga | |
| 4,954,544 A | 9/1990 | Chandaria | |
| 5,525,254 A | 6/1996 | Reininger | |
| 6,645,930 B1 | 11/2003 | Wallis et al. | |
| 7,354,889 B2 | 4/2008 | Askill | |
| 2005/0025988 A1 | 2/2005 | Wisnudel et al. | |
| 2008/0064604 A1 | 3/2008 | Melker | |
| 2008/0146479 A1 | 6/2008 | Dufresne et al. | |
| 2008/0146480 A1 | 6/2008 | Dufresne et al. | |
| 2008/0206715 A1 | 8/2008 | Kawamoto et al. | |

*Primary Examiner*—Alexander Markoff
(74) *Attorney, Agent, or Firm*—Cardinal Law Group; Ronald E. Andermann

(57) ABSTRACT

An adhesive removal indicator system and method of use including a method for removing a residual bonding adhesive from a substrate, such as human skin, the method including applying an adhesive adsorbable colored dye on the residual bonding adhesive to form a colored adhesive; applying a bonding adhesive solvent on the colored adhesive; and removing from the substrate the colored adhesive with the bonding adhesive solvent, wherein the adhesive adsorbable colored dye is a skin impermeable dye.

17 Claims, 3 Drawing Sheets

ADHESIVE REMOVAL INDICATOR SYSTEM AND METHOD OF USE

TECHNICAL FIELD

The field of this disclosure is adhesive removal, and more specifically, an adhesive removal indicator system and method of use.

BACKGROUND

Hairpieces, weaves, lace front, and full lace wigs are often applied to the scalp or existing hair on the head or to the perimeter skin around the hair line (forehead), of a person for cosmetic reasons or for aesthetic reasons, such as temporarily covering natural hair that may be thinning, breaking, or lost due to medical or health conditions. Hairpieces are made from natural hair, synthetic, or mono-filament fibers, which are attached to a base. The base, which is commonly referred to as a cap or lace, maintains the shape of the hairpiece and helps to hold the hairpiece in place on the head. The cap or lace is attached to the forehead between the hairline and face with either double stick tape or liquid adhesives (glue). When a liquid adhesive is used, the liquid adhesive is applied to the perimeter scalp or skin around the hair line (forehead), and allowed to dry or partially cure until the adhesive becomes sticky or tacky. The adhesives commonly used for the attachment of hairpieces are bonding adhesives, such as acrylate-based or silicone-based adhesives, which are preferably clear and colorless to avoid detracting from the natural appearance of the hairpiece and to avoid the appearance that a hairpiece is being used. The lace or cap is then attached to the scalp or the perimeter scalp or skin around the hair line (forehead), with partially cured bonding adhesive.

After one to four weeks, the lace of the wig is removed with lace wig remover. First, lace wig remover is applied to the lace to loosen the wig so the lace can be removed from the scalp. Unfortunately, bonding adhesive residue from the lace is left on the perimeter scalp or skin around the hair line (forehead) after the hairpiece is removed. This bonding adhesive residue, which is often clear or colorless, is difficult to detect with the naked eye, but can be felt or discovered when trying to attach a new lace wig unit. Bonding adhesive for keeping the lace wigs in place include, but are not limited to, acrylic acrylates and the condensation product of a silanol endblocked polydimethylsiloxane (PDMS) with a silicate resin. One problem with the residual bonding adhesive is that the residual adhesive on the scalp or forehead prevents cleaning of the perimeter scalp or skin around the hair line (forehead), beneath the residual bonding adhesive. Another problem with the residual bonding adhesive is that the residual bonding adhesive may interfere with attachment of another hairpiece, wig or weave at a later time. While adhesive removal indicator systems are known for the removal of residual adhesive from hard surfaces such as surfaces of cars, trucks, buses, airplanes, and so forth, such surfaces are nonadsorbent. Thus, the absorbance of system components, such as solvent and dye, is of no concern. Further, water based systems or low molecular weight hydrocarbon systems are known to be ineffective for the removal of adhesive from hard surfaces. Unfortunately, adsorbent soft surfaces that by their very nature are semipermeable, such as scalp and skin, adsorb various components of the adhesive removal indictor system. More specifically, solvents and dyes in the adhesive removal system are adsorbed into soft surfaces and can result in the staining or degradation of the soft surface, particularly if the soft surface is skin. Dye adsorption by both the residual adhesive and the substrate can make identification of the dyed residual adhesive difficult and can result in staining of the substrate.

It would be desirable to have a bonding adhesive removal indicator system and method of use to overcome the above disadvantages.

SUMMARY OF THE INVENTION

One aspect of the invention provides a method for removing a residual bonding adhesive from a substrate, the method includes applying an adhesive adsorbable colored dye on the residual bonding adhesive to form a colored bonding adhesive; then applying a bonding adhesive solvent on the colored bonding adhesive; removing from the substrate the colored bonding adhesive with the bonded adhesive solvent; and wherein the adhesive adsorbable colored dye is a skin impermeable dye.

Another aspect of the invention provides a method for removing a residual bonding adhesive from a substrate, the method includes dispersing an adhesive adsorbable colored dye throughout a mixture of a bulk solvent and a bonding adhesive solvent to form a dye colored solution; applying the dye colored solution on the residual bonding adhesive; removing the applied dye colored solution and the residual bonding adhesive from the substrate; wherein the adhesive adsorbable colored dye is a skin impermeable dye.

Another aspect of the invention provides a system for removing a residual bonding adhesive from a substrate; the system includes a bonding adhesive solvent; and a solution consisting essentially of an adhesive adsorbable colored dye dispersed throughout a bulk solvent. The solution is operable to dye the residual bonding adhesive, the bonding adhesive solvent is operable to dissolve the residual bonding adhesive, and the adhesive adsorbable colored dye is a skin impermeable dye.

DETAILED DESCRIPTION

Figure 1:
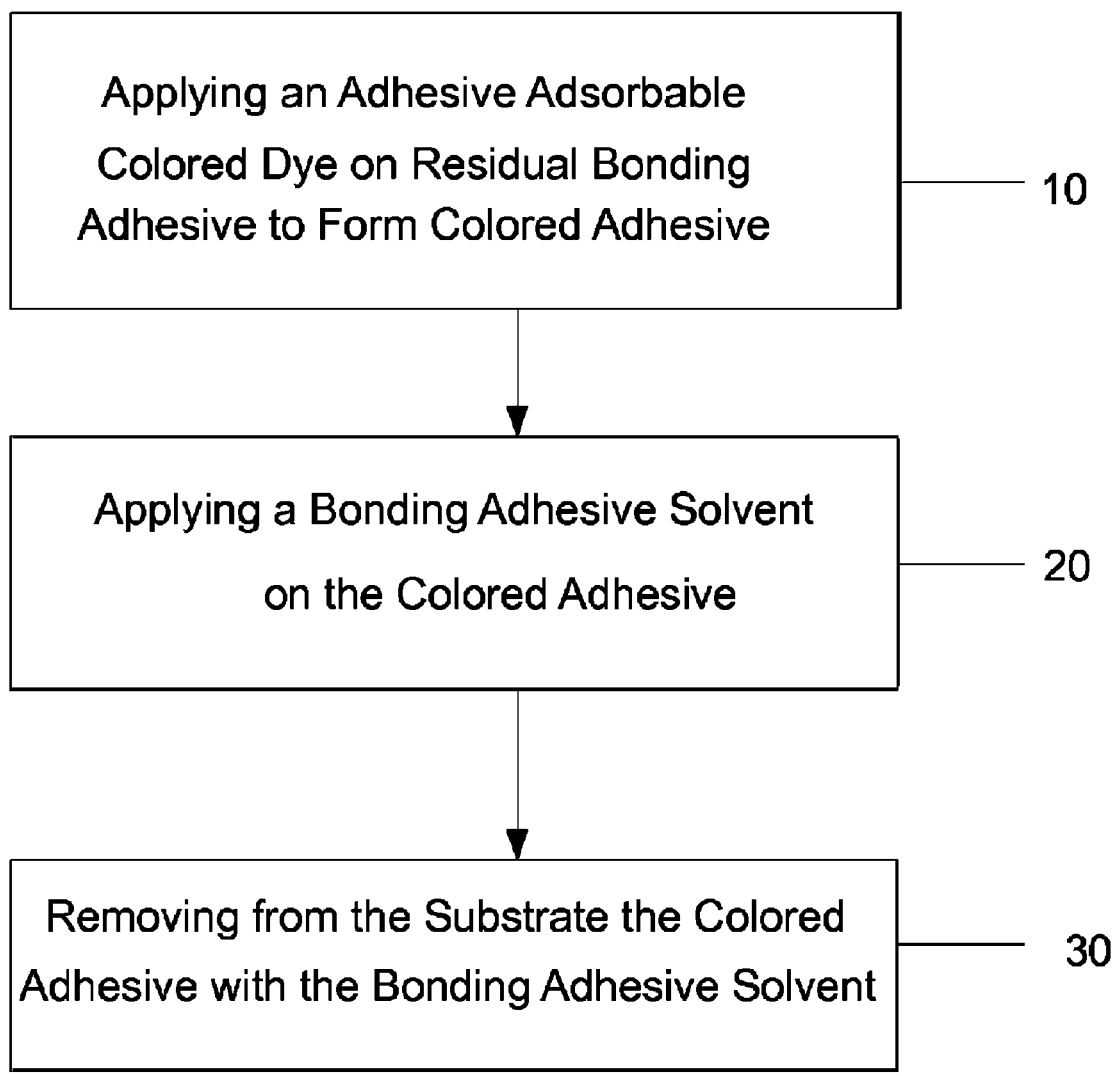
FIG. 1 is a flow chart of the method for removing residual bonding adhesive from a substrate in accordance with the present invention.

FIG. 1 is a flow chart of the method for removing residual bonding adhesive from a substrate in accordance with the present invention. The method 100 includes applying an adhesive adsorbable colored dye on the residual bonding adhesive to form a colored adhesive 10; applying a bonding adhesive solvent on the colored adhesive 20; and removing from the substrate the colored adhesive with the bonding adhesive solvent 30.

The residual bonding adhesive can be a clear/colorless bonding adhesive, such as a bonding adhesive used to attach the lace of a wig, and the substrate can be the perimeter scalp or skin around the hair line (forehead), to which the lace is attached. As commonly known, skin is a natural layer covering the body of animals generally and human specifically. Scalp is the skin on the top of the head which can include hair. Skin forms an external protective membrane or covering of the body and consists of layers known as the dermis and epidermi. The skin layers form a semi-permeable surface that protects the animal from the environment. Because skin is semi-permeable it's function as a barrier is not absolute and the transepidermal movement and adsorbtion of various chemical compounds including dyes is well known, for example tattoo inks and dyes. The applying of an adhesive adsorbable colored dye on the residual bonding adhesive 10 forms a colored bonding adhesive that is visible to the eye, so that the residual bonding adhesive can be distinguished from the substrate. In one embodiment, the adhesive adsorbable colored dye is a skin impermeable dye, i.e., the adhesive adsorbable colored dye is selectively adsorbed into the residual bonding adhesive, so that the adhesive adsorbable colored dye stains the residual bonding adhesive and makes the dyed residual bonding adhesive distinguishable over the substrate without significantly adsorbing into and staining the substrate such as skin. Without being bound by any particular theory, the skin impermeable dye is thought to be an ephemeral acting dye which is temporarily adsorbed into the semi-permeable skin layers, and then readily released, particularly by substrate cleaning with solvent or water washing. Alternately, the skin impermeable dye may just not be adsorbed in significant amounts by the semi-permeable skin. In this situation, any trace dye amounts that are permanently adsorbed are in quantities so low that the dye is not visually detectable so that the substrate does not appear to be stanined. Other less desirable permeable dyes are permanently adsorbed so as to produce visually noticeable change in the substrate. Exemplary skin impermeable dyes include Red 33, Basic Red 51, Basic Blue 99, Ebony, and the like. In another embodiment, the adhesive adsorbable colored dye is one or more of the following dyes: Red 17, Red 28, Orange 4, Yellow 11, Green 3, Green 6, and Violet 2. In another embodiment, the adhesive adsorbable colored dye includes an organomodified siloxane, such as di-Me, 3-3-(3-coco amidopropyl)dimethylammonio-2-hydroxypropoxypropyl group-terminated, acetates (salts) or the like, with skin impermeable dyes such as Red 28, Red 33, Basic Red 51, Orange 4, Yellow 5, Yellow 10, Basic Yellow 57, Acid Yellow 23, Basic Blue 3, Basic Blue 99, Green 3, Green 5, Brown 1, Ebony, Covariane Blue W 6122 (HC Blue 2), Covariane Poupre W5121 (N,N'-Bis (2-hydroxyethyl)-2nitro-p-phenylenediamine), Covariane Jaune W1122 (HC Yellow 2), and the like. It is believed that organomodified siloxanes enhances dye adsorption into the residual adhesive so that the dyed residual adhesive can be more easily identified even if some dye is adsorbed into the skin.

The applying of a bonding adhesive solvent on the colored adhesive 20 dissolves and softens the colored adhesive. In one embodiment, the bonding adhesive solvent is isopropyl alcohol, ethyl alcohol, methyl acetate, ethyl acetate, n-propyl lactate, heptane, hexamethyl disiloxane, or the like. In another embodiment, the bonding adhesive solvent includes a bulk solvent, such as isopropyl alcohol, ethyl alcohol, heptane, ethyl lactate, n-propyl lactate, water (including water mixtures having triethanolamine), or the like. In another embodiment, the bonding adhesive solvent includes a fragrance.

Solvent systems that can include either a bonding adhesive solvent and/or a bulk solvent are generally characterized as aqueous-based liquids or organic-based liquids. Aqueous-based liquids are water based formulations that can include other water soluble components such as triethanolamine, quaternary amines, water soluble dyes, and so forth. Typically, the water content is at least a quarter of aqueous-based liquid with some embodiments having greater than ninety percent water content. An aqueous-based liquid can also include other water soluble inorganic compounds such as ammonia. In contrast to aqueous-based liquids, organic-based liquids are typically hydrocarbon based formulations that are made up of generally oil soluble components such as heptane. Typically organic compounds such as hydrocarbons make up over half of organic-based liquids with some embodiments being greater than ninety percent organic compounds. An organic-based liquid can also include other oil soluble compounds such as ethyl lactate, n-propyl lactate, hexamethyl disiloxane, oil soluble dyes, and so forth.

Removing from the substrate the colored bonding adhesive with the bonding adhesive solvent 30 clears the residual bonding adhesive from the substrate.

Figure 2:
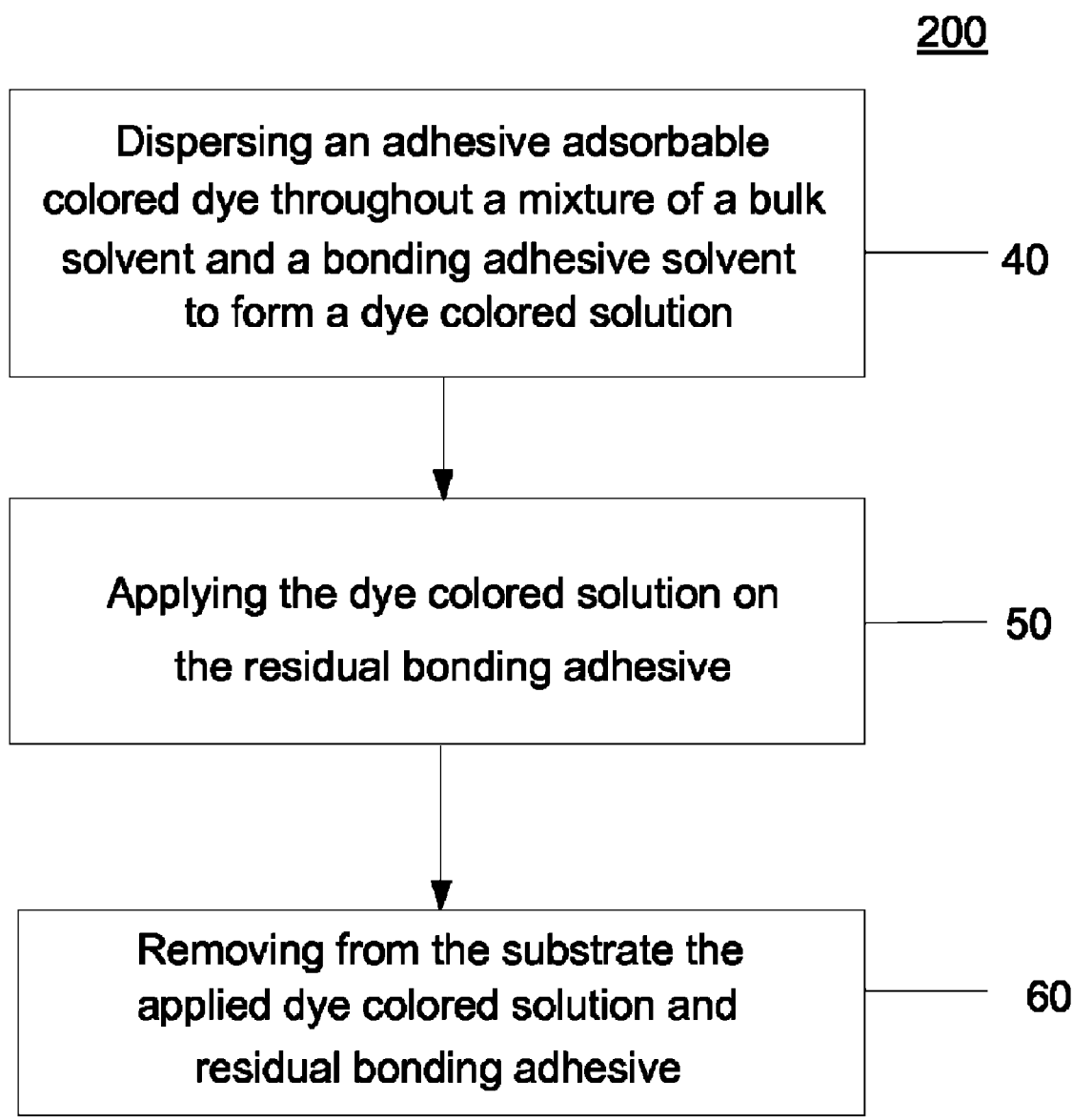
FIG. 2 is a flow chart of another embodiment of the method for removing bonding adhesive from a substrate in accordance with the present invention.

FIG. 2 is a flow chart of another embodiment of the method for removing bonding adhesive from a substrate in accordance with the present invention. The method 200 includes dispersing an adhesive adsorbable colored dye throughout a mixture of a bulk solvent and a bonding adhesive solvent to form a dye colored solution 40; applying the dye colored solution on the residual bonding adhesive 50; and removing the applied dye colored solution and the residual bonding adhesive from the substrate 60.

The residual bonding adhesive can be a clear/colorless bonding adhesive, such as a bonding adhesive used to attach the lace of a wig, and the substrate can be the perimeter scalp around the hair line (forehead) or skin to which the lace is attached. Bonding adhesive includes, but is not limited to acrylate adhesives, such as acrylic acrylates, cynoacrylates, and vinyl acetate monomers. and silicone adhesives such as the condensation product of a silanol endblocked polydimethylsiloxane (PDMS) (Dow Corning® MD7-4502) with a silicate resin. The dispersing of an adhesive adsorbable colored dye throughout a mixture of a bulk solvent and a bonding adhesive solvent 40 forms a dye colored solution. In one embodiment, the adhesive adsorbable colored dye is a skin impermeable dye, i.e., the bonding adsorbable colored dye is selectively adsorbed into the residual bonding adhesive, so that the adhesive adsorbable colored dye stains the residual bonding adhesive without significantly adsorbing into and staining the substrate. In another embodiment, the adhesive adsorbable colored dye is one or more of the following dyes: Red 17, Red 28, Red 33, Basic Red 51, Orange 4, Yellow 1, Yellow 5, Yellow 11, Basic Yellow 57, Acid Yellow 23, Blue 1, Basic Blue 3, Basic Blue 99, Green 3, Green 5, Green 6, and Violet 2. In yet another embodiment, the adhesive adsorbable colored dye includes an organomodified siloxane, such as di-Me, 3-3-(3-coco amidopropyl)dimethylammonio-2-hydroxypropoxypropyl group-terminated, acetates (salts) or the like.

Those skilled in the art will appreciate that the bulk solvent and bonding adhesive solvent in the mixture can be selected as desired for a particular application, considering such factors as compatibility with other materials. In one embodiment, the bulk solvent is isopropyl alcohol, ethyl alcohol, heptane, ethyl lactate, n-propyl lactate, triethanolamine, water, or the like. In another embodiment, the bonding adhesive solvent is methyl acetate, ethyl acetate, n-propyl lactate, heptane, hexamethyl disiloxane, or the like. In yet another embodiment, the mixture also includes a fragrance.

Applying of the dye colored solution on the residual bonding adhesive 50 makes the residual bonding adhesive visible against the substrate so the user can identify and remove the residual bonding adhesive. Removing of the applied dye colored solution from the residual bonding adhesive 60 clears the residual bonding adhesive from the substrate.

The method of removing the residual bonding adhesive from the substrate can be practiced with a system including a bonding adhesive solvent and a solution consisting essentially of an adhesive adsorbable colored dye dispersed throughout a bulk solvent. The solution dyeing the residual bonding adhesive and the bonding adhesive solvent is operable to dissolving the residual bonding adhesive.

Figure 3:
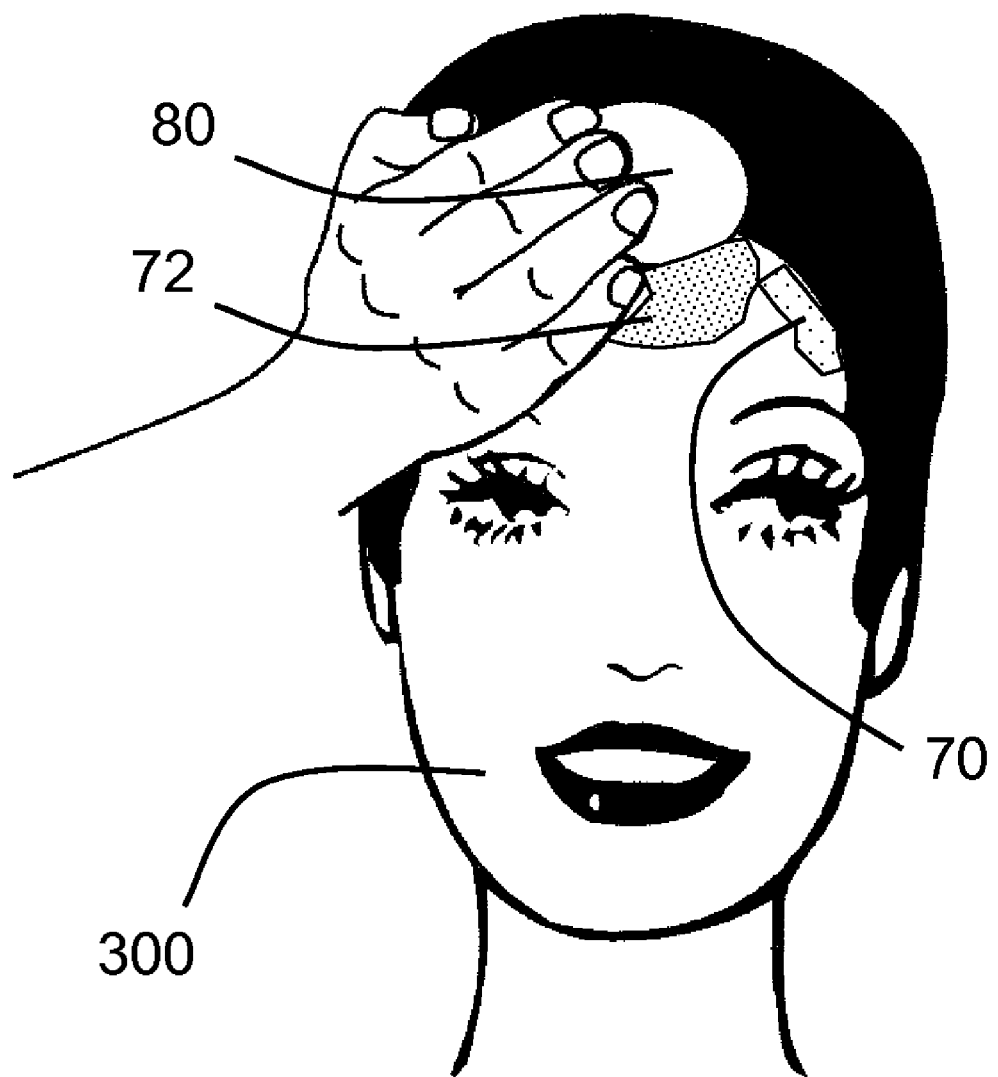
FIG. 3 is a schematic diagram of the practice of a method for removing residual bonding adhesive from a substrate in accordance with the present invention.

FIG. 3 is a schematic diagram of the practice of a method for removing residual bonding adhesive from a substrate in accordance with the present invention. A person can remove a residual bonding adhesive, such as a clear/colorless bonding adhesive or the like used to attach the lace of a wig, from a substrate, such as the skin, forehead, scalp, or the like, to which the lace is attached. The method can employ an adhesive adsorbable colored dye or a dye colored solution to make the residual bonding adhesive visible for removal.

When employing an adhesive adsorbable colored dye, the person 300 or someone assisting the person 300 first removes the hairpiece, such as a lace wig unit, using a hairpiece remover solvent. An adhesive adsorbable colored dye is applied to the residual bonding adhesive 70 remaining on the scalp or the perimeter skin around the hair line (forehead) of the person 300. The adhesive adsorbable colored dye is selectively adsorbed into the residual bonding adhesive 70 over a desired time, such as 10 to 25 seconds, for example. In one embodiment, the adhesive adsorbable colored dye is a skin impermeable dye, which is adsorbed into and does not significantly color the skin of the scalp and/or face. The adhesive adsorbable colored dye makes the residual bonding adhesive 70 visible for removal as colored adhesive 72. A bonding adhesive solvent, such as methyl acetate, ethyl acetate, n-propyl lactate, heptane, hexamethyl disiloxane, or the like, is applied to the colored adhesive 72. The bonding adhesive solvent can be applied to the colored adhesive 72 with an applicator 80, such as a cotton ball, small cloth, cotton rounds, or cotton-tip swab. The bonding adhesive solvent penetrates and dissolves the colored adhesive 72 over a desired time. Light rubbing on the colored adhesive 72 with the solvent soaked applicator 80 continues until the colored adhesive 72 is removed from the perimeter scalp or skin around the hair line (forehead) or skin. The colored adhesive 72 is visible due to the bonding adhesive adsorbable dye, so visual examination by the person 300 readily determines when the colored adhesive 72 has been removed from the skin.

When employing a dye colored solution, the person 300 or someone assisting the person 300 first removes the hairpiece, such as a lace wig unit, using a hairpiece remover solvent. A dye colored solution, which can include an adhesive adsorbable colored dye dispersed throughout a mixture of a bulk solvent and a bonding adhesive solvent, is applied to the residual bonding adhesive 70 remaining on the scalp of the person 300. The dye colored solution makes the residual bonding adhesive 70 visible as colored adhesive 72. The dye colored solution is selectively adsorbed into the residual bonding adhesive 70 over a desired time, such as 10 to 25 seconds, for example. In one embodiment, the adhesive adsorbable colored dye in the dye colored solution is a skin impermeable dye, which is adsorbed into and does not significantly color the skin of the scalp and/or face. The adhesive adsorbable colored dye can be Red 17, Red 28, Basic Red 51, Orange 4, Yellow 5, Yellow 10, Yellow 11, Basic Yellow 57, Acid Yellow 23, Blue 1, Basic Blue 3, Basic Blue 99, Green 3, Green 5, Green 6, and Violet 2 or the like. The bulk solvent can be isopropyl alcohol, ethyl alcohol, heptane, ethyl lactate, n-propyl lactate, triethanolamine, water, or the like. The bonding adhesive solvent can be methyl acetate, ethyl acetate, n-propyl lactate, heptane, hexamethyl disiloxane, or the like.

The dye colored solution can be applied to the residual bonding adhesive 70 with an applicator 80, such as a cotton ball, small cloth, cotton rounds, or cotton-tip swab. The bonding adhesive solvent in the dye colored solution penetrates and dissolves the residual bonding adhesive 70 over a desired time. Light rubbing on the colored adhesive 72 with the solvent soaked applicator 80 continues until the applied dye colored solution and the residual bonding adhesive is removed from the skin. The colored adhesive 72 is visible due to the bonding adhesive colored dye, so visual examination by the person 300 readily determines when the residual bonding adhesive 72 has been removed from the skin.

Application and Use

The embodiments discussed above provide a system and method for indicating the presence of residual bonding adhesive, particularly clear and colorless residual bonding adhesive, to aid in removal of the residual bonding adhesive. The bonding adhesive adsorbable dyes are adsorbed into and stain the bonding adhesive. In one embodiment, the bonding adhesive adsorbable dyes are adsorbed by the residual bonding adhesive and are either not adsorbed by the substrate or have limited adsorption. For situations when some dye is adsorbed by the substrate and depending on the specific dye, the dye can be reversibly desorbed from the substrate by the application of solvent including, but not limited to water washing. The adhesive staining intensity can vary depending on the specific composition of the residual bonding adhesive and the bonding adsorbable dyes. In one embodiment, the bonding adhesive adsorbable dyes are not significantly adsorbed by skin and do not stain the skin.

Formulations

Those skilled in the art will appreciate that the adhesive adsorbable colored dye discussed herein can be any suitable dye which can be adsorbed by the bonding adhesive without being significantly adsorbed by the substrate. Bonding adhesives include, but are not limited to, acrylic acrylates, cynoacrylates, and the condensation product of a silanol end-blocked polydimethylsiloxane (PDMS) with a silicate resin (such as Dow Corning® MD7-4502 silicone adhesive). Suitable adhesive adsorbable colored dyes include, but are not limited to, Red 17, Red 28, Red 33, Basic Red 51, Orange 4, Yellow 5, Yellow 10, Yellow 11, Basic Yellow 57, Acid Yellow 23, Basic Blue 3, Basic Blue 99, Green 3, Green 5, Green 6, Violet 2, and Brown 1. Additional additives such as can be used to aid in the dispersion of the adhesive adsorbable colored dye. Organomodified siloxanes such as, di-Me, 3-3-(3-coco amidopropyl)dimethylammonio-2-hydroxypropoxypropyl group-terminated, acetates (salts) (Quaternium-80) can be included with the adhesive adsorbable colored dye to improve adsorption of the adhesive adsorbable colored dye in the residual bonding adhesive.

The adhesive adsorbable colored dye can be mixed with a bulk solvent such as isopropyl alcohol, ethyl alcohol, or the like, or an adhesive solvent, such as methyl acetate, ethyl lactate, n-propyl lactate, heptane, hexamethyl disiloxane, or mixed with di-Me, 3-3-(3-coco amidopropyl)dimethylammonio-2-hydroxypropoxypropyl group-terminated, acetates (salts). In addition, the adhesive adsorbable colored dye and optional organomodified siloxanes can be formulated with other thickening agents into mixtures such as pastes to form part of a stick, cotton swab, or fabric pad, in which the adhesive adsorbable colored dye mixture is stored in the stick, cotton swab, or fabric pad.

Those skilled in the art will appreciate that the above mentioned mixtures can further include UV stabilizers, such as hydroxybenzoyl hexyl benzoate, or skin emollients and/or moisturizers such as ethylhexly methoxycinnamate.

EXPERIMENTAL RESULTS

Example 1

Samples were prepared using standard lace wig adhesive (Salon Pro 30 Sec. Extreme Hold Lace Wig Bond) applied to glass plates at room temperature. Two inch by two inch samples of adhesive were applied to the glass plate with eight adhesive samples per plate and were allowed to cure overnight. Samples of the specified dye 0.10% were added to deionized water 92.90%, organomodified siloxanes 3% (Abil® Quat 3474) and triethanolamine (TEA) 4.00% and mixed to form an aqueous-based dye formulation. A sample of each aqueous-based dye formulation was applied to the adhesive samples. The dye formulation was left on the adhesive sample for 30 seconds and rinsed off; with the result that all dye formulations stained the adhesive samples. The following dyes were tested: Red 17, Red 28, Red 33, Basic Red 51, Orange 4, Yellow 5, Yellow 10, Yellow 11, Basic Yellow 57, Acid Yellow 23, Basic Blue 3, Basic Blue 99, Green 3, Green 5, Green 6, and Violet 2, Brown 1, Ebony, Covariane Blue W 6122 (HC Blue 2), Covariane Poupre W5121 (N,N'-Bis (2-hydroxyethyl)-2nitro-p-phenylenediamine), and Covariane Jaune W1122 (HC Yellow 2). Appreciable dye residue, as required to detect the presence of the residual adhesive, was detected in the adhesive for the following dyes which separately did not noticeably stain skin: Red 28, Red 33, Basic Red 51, Orange 4, Yellow 5, Yellow 10, Basic Yellow 57, Acid Yellow 23, Basic Blue 3, Basic Blue 99, Green 3, Green 5, Brown 1, Ebony, Covariane Blue W 6122, Covariane Poupre W5121, and Covariane Jaune W1122.

Example 2

A second set of samples were prepared using standard lace wig adhesive (Salon Pro 30 Sec. Extreme Hold Lace Wig Bond) applied to glass plates at room temperature as in Example 1. Two inch by two inch samples of adhesive were applied to the plate with a total of eight adhesive samples per plate. The adhesive samples were allowed to cure overnight. Samples of the specified dye 0.01% was added to methyl acetate 10.00%, ethyl acetate 10.00%, n-propyl lactate 10.00%, heptane 18.00% hexamethyl disiloxane 51.89% and fragrance 0.10% The various organic-based liquids were mixed and samples of each dye and solvent formulation were placed on separate adhesive samples. The dye sample were left on the adhesive for 30 seconds and rinsed off. All samples dyed the adhesives. The following dyes were tested: Red 17, Red 28, Basic Red 51, Orange 4, Yellow 11, Green 3, Green 6, Violet 2, Ebony, Covariane Blue W 6122 (HC Blue 2), Covariane Poupre W 5121 (N,N'-Bis (2-hydroxyethyl)-2nitro-p-phenylenediamine), and Covariane Jaune W1122 (HC Yellow 2). Appreciable dye residue, as required to detect the presence of the residual adhesive, was detected in the adhesive for the following dyes which separately did not noticeably stain skin: Red 17, Red 28, Orange 4, Yellow 11, Green 3, Green 6, and Violet 2.

Example 3

Another set of samples were prepared using standard lace wig adhesive (Salon Pro 30 Sec. Extreme Hold Lace Wig Bond) was applied to a glass plates at room temperature as in Example 1. Two inch by two inch samples of adhesive were applied to the plate with a total of eight adhesive samples per plate. The adhesive samples were allowed to cure overnight. Samples of the specified dye 0.1% were added to and mixed to deionized water 94.9%, triethanolamine 5.0%. The liquids were mixed and samples of each aqueous-based dye formulation were placed on separate adhesive samples. The dye sample were left on the adhesive for 30 seconds and rinsed off. The following dyes were tested: Ebony, Basic Blue No. 3, Basic Blue No. 99, Red 33, Basic Red 51, Covariane Blue W 6122 (HC Blue No. 2), Covariane Poupre W 5121 (N,N'-Bis (2-hydroxyethyl)-2nitro-p-phenylenediamine), and Covariane Jaune W1122 (HC Yellow No. 2). Appreciable dye residue, as required to detect the presence of the residual adhesive, was detected in the adhesive for the following dyes which separately did not noticeably stain skin: Ebony, Basic Blue No. 99, Red 33, and Basic Red 51.

While the embodiments of the invention disclosed herein are presently considered to be preferred, various changes and modifications can be made without departing from the scope of the invention. The scope of the invention is indicated in the appended claims, and all changes that come within the meaning and range of equivalents are intended to be embraced therein.

The invention claimed is:

1. A method for removing a residual bonding adhesive from a substrate, the method comprising:
   providing the residual bonding adhesive on the substrate, wherein the residual bonding adhesive results from the application of adhesive to the substrate;
   applying an adhesive adsorbable colored dye on the residual bonding adhesive to form a colored adhesive;
   applying a bonding adhesive solvent on the colored adhesive;
   removing from the substrate the colored adhesive with the bonding adhesive solvent;
   wherein the substrate is selected from the group consisting of: skin, scalp, hair, forehead, hairline, epidermis, and combinations thereof; and
   wherein the adhesive adsorbable colored dye is a skin impermeable dye.

2. The method of claim 1, wherein the adhesive adsorbable colored dye further comprises an organomodified siloxane.

3. The method of claim 1, wherein the adhesive adsorbable colored dye is dispersed in an aqueous-based liquid.

4. The method of claim 3, wherein the adhesive adsorbable colored dye is selected from the group consisting of Red 33, Basic Red 51, Basic Blue 99, and Ebony.

5. The method of claim 3, wherein the adhesive adsorbable colored dye further comprises an organomodified siloxane.

6. The method of claim 5, wherein the organomodified siloxane is di-Me, 3-3-(3-coco amidopropyl)dimethylammonio-2-hydroxypropoxypropyl group-terminated, acetates (salts).

7. The method of claim 5, wherein the adhesive adsorbable colored dye is selected from the group consisting of Red 28, Red 33, Basic Red 51, Orange 4, Yellow 5, Yellow 10, Basic Yellow 57, Acid Yellow 23, Basic Blue 3, Basic Blue 99, Green 3, Green 5, Brown 1, Ebony, Covariane Blue W 6122, Covariane Poupre W5121, and Covariane Jaune W1122.

8. The method of claim 1, wherein the bonding adhesive solvent is selected from the group consisting of methyl acetate, isopropyl alcohol, ethyl alcohol, ethyl acetate, n-propyl lactate, heptane, and hexamethyl disiloxane.

9. The method of claim 1, wherein the adhesive adsorbable colored dye is dispersed in an organic-based liquid.

10. The method of claim 9, wherein the adhesive adsorbable colored dye is selected from the group consisting of Red 17, Red 28, Orange 4, Yellow 11, Green 3, Green 6, and Violet 2.

11. A method for removing a residual bonding adhesive from a substrate, the method comprising:
providing the residual bonding adhesive on the substrate, wherein the residual bonding adhesive results from the application of adhesive to the substrate;
dispersing an adhesive adsorbable colored dye throughout a mixture of a bulk solvent and a bonding adhesive solvent to form a dye colored solution;
applying the dye colored solution on the residual bonding adhesive; removing from the substrate the applied dye colored solution and the residual bonding adhesive;
wherein the substrate is selected from the group consisting of: skin, scalp, hair, forehead, hairline, epidermis, and combinations thereof; and
wherein the adhesive adsorbable colored dye is a skin impermeable dye.

12. The method of claim 11, wherein the mixture is an aqueous-based liquid.

13. The method of claim 12, wherein the adhesive adsorbable colored dye further comprises an organomodified siloxane.

14. The method of claim 13, wherein the organomodified siloxane is di-Me, 3-3-(3-coco amidopropyl)dimethylammonio-2-hydroxypropoxypropyl group-terminated, acetates (salts).

15. The method of claim 13, wherein the adhesive adsorbable colored dye is selected from the group consisting of Red 28, Red 33, Basic Red 51, Orange 4, Yellow 5, Yellow 10, Basic Yellow 57, Acid Yellow 23, Basic Blue 3, Basic Blue 99, Green 3, Green 5, Brown 1, Ebony, Covariane Blue W 6122, Covariane Poupre W5121, and Covariane Jaune W1122.

16. The method of claim 11, wherein the bonding adhesive solvent is selected from the group consisting of methyl acetate, ethyl acetate, n-propyl lactate, heptane, and hexamethyl disiloxane.

17. The method of claim 11, wherein the bulk solvent consists essentially of heptane, ethyl lactate, and n-propyl lactate; the bonding adhesive solvent consists essentially of heptane and hexamethyl disiloxane; and the adhesive adsorbable colored dye consists essentially of Red 17.

* * * * *